(12) United States Patent
Lacey

(10) Patent No.: US 6,459,757 B1
(45) Date of Patent: Oct. 1, 2002

(54) X-RAY DETECTOR ARRAY WITH PHASE CHANGE MATERIAL HEAT SYSTEM

(75) Inventor: Joseph J. Lacey, Cambridge, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/683,917

(22) Filed: Mar. 1, 2002

(51) Int. Cl.[7] ............................................... G01N 23/00
(52) U.S. Cl. ............................................. 378/19; 378/4
(58) Field of Search .................... 378/4–20; 250/370.09

(56) References Cited

U.S. PATENT DOCUMENTS 6,249,563 B1    6/2001    Snyder et al.

*Primary Examiner*—Craig E. Church
(74) *Attorney, Agent, or Firm*—Quarles & Brady LLP

(57) ABSTRACT

Disclosed is an X-ray detector assembly for use in a computed tomography system. The X-ray detector assembly comprises an array of detector cells coupled between two rails. A phase change material is coupled to each of the rails, and is controlled by a heater element to maintain the phase change material, and hence the detector array, in a substantially isothermal condition.

18 Claims, 5 Drawing Sheets

X-RAY DETECTOR ARRAY WITH PHASE CHANGE MATERIAL HEAT SYSTEM

BACKGROUND OF THE INVENTION

The present invention is generally directed to an X-ray detector array for use in a computed tomography system, and more particularly to a method and apparatus for maintaining an X-ray detector array in a substantially isothermal condition.

A computed tomography (CT) imaging system typically includes an x-ray source and an x-ray detector array mounted on opposite sides of a gantry with an imaging area interposed between. The detector array typically includes a plurality of detector elements arranged in rows and columns. The detector array or module includes the detection elements and associated electrical components to convert the x-ray signal to either a measurable analog or quantifiable digital signal. In many configurations the array is mounted to the gantry on axially separated rails.

In operation the x-ray source generates x-rays that are directed at the array. When an object (e.g., the torso of a patient) is positioned within the imaging area, x-rays passing through the object are attenuated to different degrees, the varying degrees of attenuation dependent upon characteristics of the material through which the x-rays pass within the imaging area (e.g., bone may attenuate to a greater degree than flesh, etc.).

In CT, the gantry is used to rotate the x-ray source and detector array about an object to be imaged so that data corresponding to every angle is collected. Thereafter, the collected data is filtered, weighted and typically back projected by an image processor to generate one or more diagnostic quality images.

In image reconstruction, it is assumed that the gain of each detector remains constant throughout a data acquisition process and that any change in x-ray signal intensity at the detector is due to patient anatomy. Unfortunately, this assumption is not 100% accurate for several reasons. One particularly acute source of error in this regard has to do with how detector element operation is affected by element conditions during operation. More specifically, as is the case with many different electronic components, detector element response to a specific stimuli (e.g., a specific intensity x-ray) varies as a function of temperature.

There are several ways in which temperature affects element output and overall accuracy of acquired data. First, not surprisingly, temperature directly affects element output (or gain). During operation the temperatures of the module can range from the calibration temperature, therefore resulting in uncorrected gain errors. Second, temperature gradients along array rails and between rails have been known to change the relative positions of the rails. Third, other detector array components (e.g., photo diode associated with detector elements), are also affected by changes in temperature. Specifically the shunt resistance of a photo diode drops exponentially with temperature which results in leakage currents and generally a decrease in the signal to noise ratio.

When array output varies as a function of element and array environment temperature, the quality of resulting images is adversely affected. To this end, it has been observed that temperature affects on array output sometimes result in image artifacts that adversely affect the diagnostic usefulness of the resulting images.

There are many sources of heat in CT systems that directly affect the temperature of the array. Specifically the X-ray tube used to generate the X-ray beam generates a large amount of heat in a CT system. In addition, motors, processors and other CT system components generate heat in the vicinity of the array. In recent years, the desire to increase patient throughput (i.e., the number of acquisition sessions performed per day) has fueled the use of more powerful x-ray sources so that the amount of data required to generate images can be acquired in a shorter period of time. These higher powered systems, while appreciably faster than their predecessors, have only exacerbated the array heating problem and the associated image degradation.

To address temperature related array operation problems, the industry has developed various solutions aimed at maintaining isothermal arrays. To this end, accepting that elements will heat during operation, most solutions provide some type of element heating configuration that is mounted with the array on the rails. The heating configuration is generally used to heat the elements approximately to an expected high temperature level and to maintain that temperature level throughout an acquisition period. The heater control point is set to be consistent with the expected high temperature limit and the maximum allowable module temperature change.

Unfortunately, the array temperatures occurring in high power systems can exceed the upper temperature bound which renders the heating configurations ineffective at maintaining an isothermal condition. In other words, when the detector temperature exceeds a target expected temperature level during some portion of an acquisition period, the heating configuration which is limited by the upper temperature bound is effectively useless. Additionally large differences in the detector environmental condition make it difficult to maintain uniform detector temperature with current heater only systems.

There remains a need, therefore, for a simple and economic method for maintaining a detector array at a constant temperature, and particularly for maintaining a detector array at a constant temperature when operated in conjunction with high-powered X-ray tubes.

SUMMARY OF THE INVENTION

An exemplary embodiment of the invention comprises a detector array, which is coupled to a phase change material, which maintains the detector array in a substantially isothermal condition. A sensor monitors the phase of the phase change material, and transmits sensed data to a controller, which selectively applies heat to the phase change material to maintain the material in a selected condition. The sensor can comprise a temperature sensor, a pressure or displacement sensor, a heat flux sensor, or various other sensors capable of monitoring the state of the phase change material.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION

Figure 1:
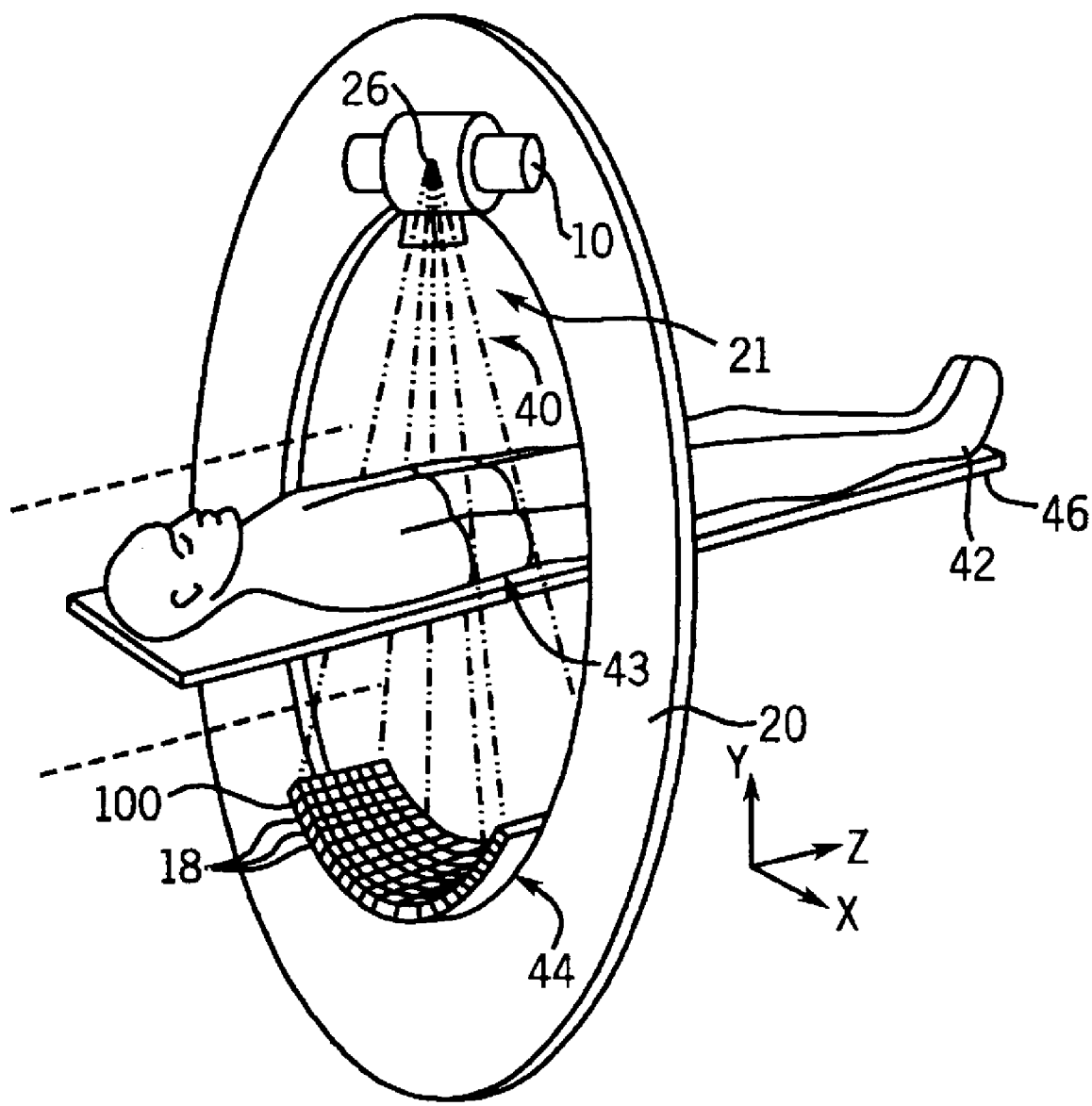
FIG. 1 is a perspective view of a CT apparatus used to practice the present invention which includes a detector array having rows and columns of detector elements and fan beam source.

Referring now to the Figures and more particularly to FIG. 1, a typical CT scanner for use in the present invention is shown. The CT scanner generally comprises a ring gantry 20 defining a central bore or imaging area 21. An X-ray source 10 is mounted opposite a detector assembly 44 on opposite sides of imaging area 21. The X-ray source 10 provides a fan beam of x-rays 40 that are directed at a portion 43 of a patient 42 resting on a support platform 46 to be scanned, and the detector assembly 44 receives the X-rays and provides intensity signals corresponding to the attenuation of the fan beam ray 40 as it passes through the object. This data is employed in image reconstruction to reconstruct one or more images of the object.

Figure 2:
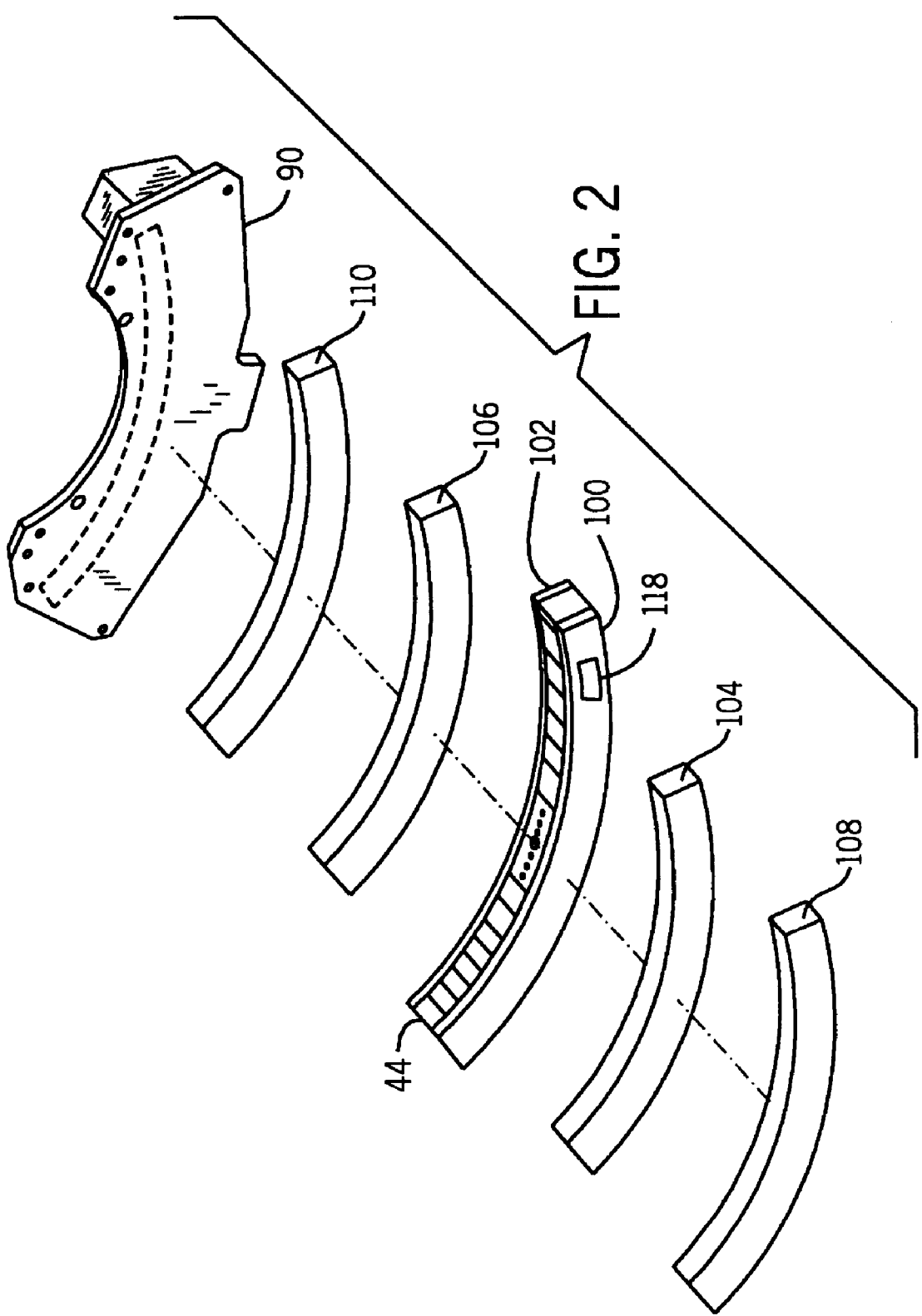
FIG. 2 is an exploded view of a detector assembly constructed in accordance with the present invention.
Figure 3:
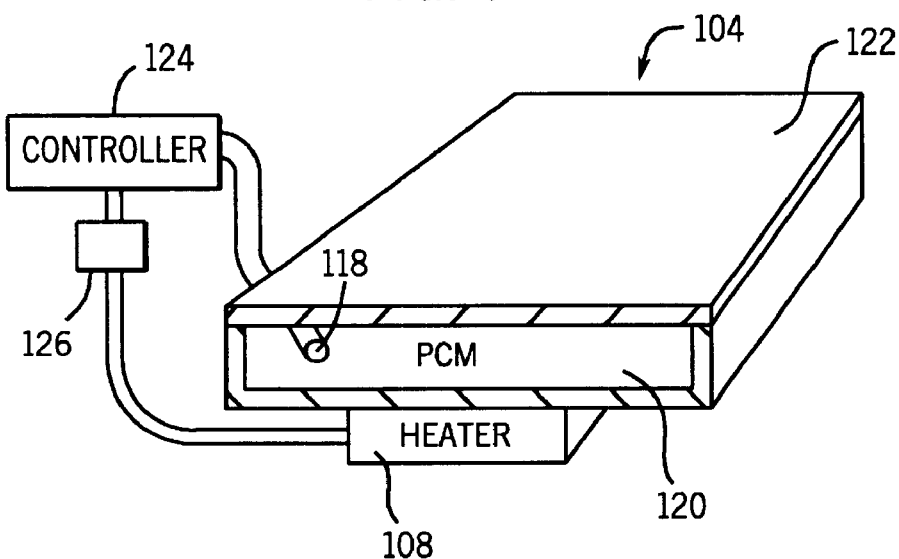
FIG. 3 is a cutaway side view of a phase control module constructed in accordance with a first embodiment of the invention.

Referring now to FIGS. 1, 2 and 3, detector assembly 44 is coupled to a mounting plate 90 which, in turn, is coupled to gantry 20 (see FIG. 1). Detector assembly 44 comprises an array of detector cells 18 coupled between first and second rails 100 and 102, respectively. Rails 100 and 102 are axially displaced along a Z or translation axis of the scanner system. Each of the detector elements 18 comprises a solid state X-ray detector as is described, for example, in commonly assigned U.S. Pat. No. 5,521,387, issued to Riedner et al. The detector elements 18 each receive x-rays and provides intensity measurements along separate rays of the fan beam 40. The detector elements 18 of the detector assembly 44 can be arranged in an arcuate configuration as shown, wherein a focal point 26 corresponds to a central point within the X-ray source. Alternatively, a focal point may correspond to the center of the gantry 20 or other locations. In some applications the detector assembly 44 may comprise a planar element. To facilitate detector assembly temperature monitoring, one or more temperature sensors 118 is embedded in detector assembly 44.

Referring still to FIG. 2, first and second temperature control modules 104 and 106 are coupled to each of the rails 100 and 102, respectively. The temperature control modules 104 and 106 comprise a phase change material which acts as a passive heat sink for maintaining the detector array 44 in a substantially isothermal condition as described below. First and second heater elements 108 and 110 are coupled to each of the temperature control modules 104 and 106, and a sensor 118, is coupled between the rails 100 and 102 and the temperature control modules 104 and 106, respectively. The heater elements 108 and 110 operate in conjunction with the temperature control modules 104 and 106, the sensor 118, and the associated temperature control modules 104 and 106 to maintain the detector array 44 at a selected operational temperature, also as described more fully below. The sensor 118 can comprise a temperature sensor (FIG. 2), a pressure sensor (FIG. 5), a strain gauge (FIG. 5), or displacement sensor (FIG. 6), a heat flux sensor (FIG. 7) or other types of sensors which can be employed to monitor the sate of the phase charge material, described below.

Referring now to FIG. 3 the temperature control module 104 comprises a phase change material 120 encased in a sealed vessel 122. The phase change material 120 can be any material capable of storing thermal energy as latent heat and capable of a phase change in the temperature range of interest, typically liquid/solid phase transitions. A number of materials exhibit this property. For example, water, wax paraffins, alcohol, eutectic salts and salt hydrates have notably high energy densities over temperature ranges of practical significance. Other materials suitable for constructing phase change material heat sinks are phenols, glycols, and starch based mixtures. In the present application a paraffin-based phase change material changing from solid to liquid in the 30–38° C. temperature range. Paraffin is preferred because as the paraffin changes from solid to liquid, it grows only about 15% in volume.

The sealed vessel 122 effectively seals the phase change material 120 from the ambient environment by providing an air and liquid impervious casing. The sealed vessel 122 preferably comprises a moisture-resistant material such as stainless steel or aluminum, resistant to corrosion from the PCM. The vessel can be sealed using threaded fasteners such as bolts, or alternatively using adhesives, weldments, or other sealing processes known to those of skill in the art.

The phase change material 120 is a passive device which requires an outside heat supply to act as an isothermal heat source. Therefore, the heater 108 is coupled to the temperature control module 104 to provide the heat source required by the phase change material. The heater 108 maintains the phase change material 120 in a phase change region between solid and liquid or liquid and vapor to provide an isothermal heat source which in turn, acts as a heat sink to the detector array 44. The heater 108 can comprise a resistance wire heater, or a positive temperature coefficient (PTC) heater which automatically changes resistance with temperature, thereby maintaining a self-regulating temperature control. Alternatively, the heater 108 can comprise a thermoelectric cooler or Peltier device, capable of providing both a heating and cooling function, depending on the polarity of the applied power source.

Referring still to FIG. 3 the heater 108 is controlled by a heater controller 124. The heater controller 124 is electrically coupled to provide an adjustable power supply to the heater 108, and is further electrically coupled to the sensor 118 which provides a signal indicative of an operating parameter of the temperature control module 104, as discussed more fully below.

Figure 4:
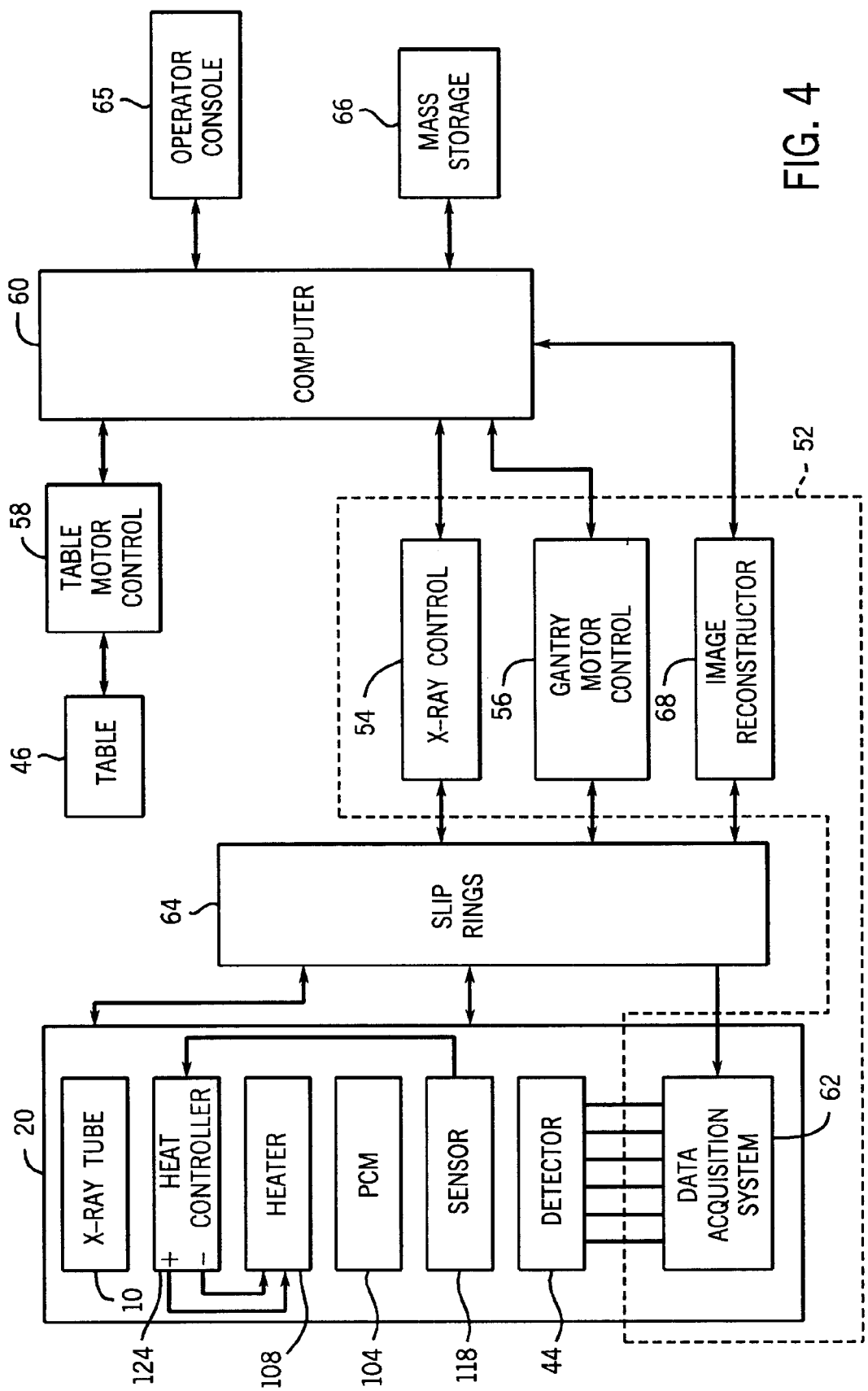
FIG. 4 is a block diagram of a CT control system which may be used to control the CT apparatus of FIG. 1 and which is useful for the purposes of practicing the present invention.

Referring now to FIG. 4, an exemplary control system for controlling the CT imaging system of FIG. 1 includes a table motor control 58, slip rings 64, a central processing computer 60, an operator's console 65, a mass storage device 66 and a plurality of control modules 52 associated with the gantry ring 20. The gantry control modules 52 include an x-ray control 54, a gantry motor control 56, a data acquisition system 62 and an image reconstructor 68. These modules are connected to the associated gantry via slip rings 64 and are linked to computer 60 for control purposes.

The gantry control modules 52 further include a heater controller 124 for controlling heater 108 to maintain detector array 44 in an isothermal condition. Heater controller 124 is preferably a commercially available device, such as the E5_N produced by Omron, but typically custom-built units are used to enable communication with the rest of the CT system. Therefore, heater controller 124 can comprise any number of devices capable of controlling heater 108 using a control method such as a proportional (P), proportional integral (PI), proportional integral derivative (PID) loop, or other methods known to those of skill in the art. Heater controller 124 is electrically coupled to sensor 118 in detector assembly 44, to a power supply to the heaters 108 and 110, and preferably to computer 60 or other device capable of establishing a set point. In all applications, the heater controller 124 can also comprise a programmable controller such as a microprocessor, a microcontroller, or other control circuitry know to those of skill in the art.

When the heaters 108 and 110 are thermoelectric coolers, the heater controller 124 controls both the polarity and the level of the power supply applied to the heaters 108 and 110. In this application, the heater controller 124 can comprise a commercially available control module associated with the thermoelectric cooler, such as Thematec™ TEC series from Melcor of Trenton, N.J. When the heater element 108 and 110 are TEC devices, the heater controller 124 can also switch the polarity of the power leads supplied to the heater elements 108 and 110, thereby switching the devices from a "heat" to a "cool" or refrigeration mode. A cooling function is particularly desirable when the ambient temperature surrounding the CT scanner is above the allowable module operating range.

In operation an object, (e.g., patient 42 resting on movable table 46) is placed within imaging area 21. The X-ray source 10 provides an X-ray fan beam 40 which is directed at the patient 42. Gantry 20 is rotated around patient 42 and image data related to a volume 43 of the patient is collected. After passing through the patient 42 the X-rays of the fan beam 40 are received by array 44.

During data acquisition, heater controller 124 maintains detector array 44 at a substantially constant temperature. A desired operational "set" point can be stored in memory, selected by a user through an interface coupled to the computer 60, established through the use of a potentiometer coupled to the heater controller or in other ways known to those of skill in the art. The selected "set" point is provided to the heater controller 124 via a control line. Heater controller 124 receives electrical signals from the sensors 118 providing indications of the actual condition of detector assembly 44 and compares these values to the "set" point. Based on the difference between the actual and desired condition, heater controller 124 adjusts the output power supplied to the heaters 108 and 110.

Figure 5:
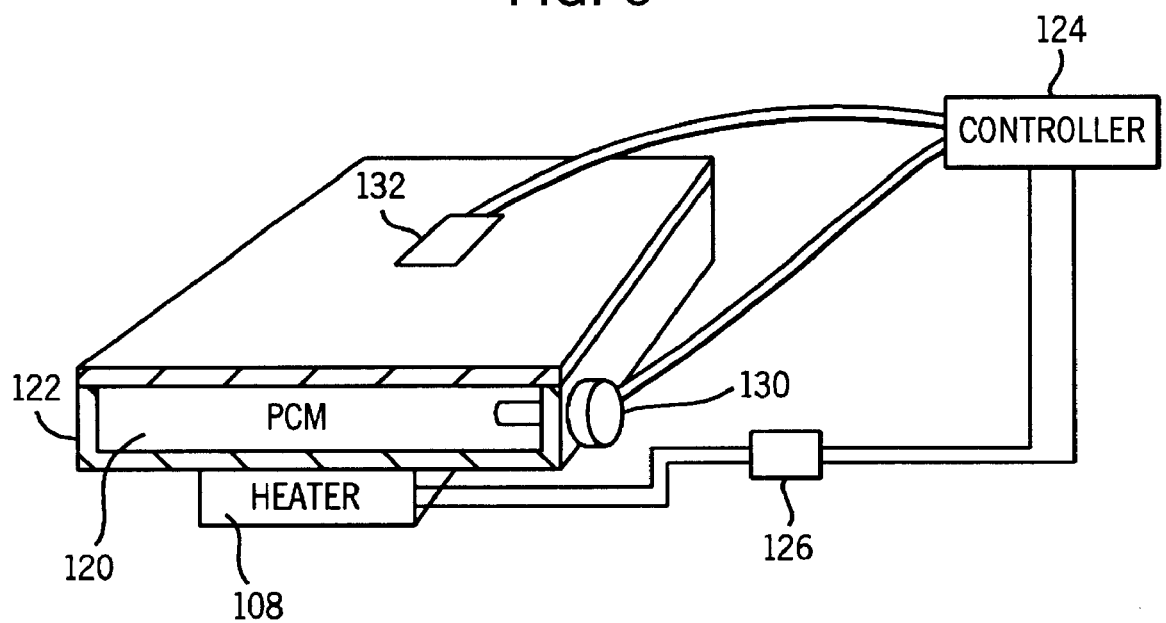
FIG. 5 is a cutaway side view of a phase control module constructed in accordance with a second embodiment of the invention.
Figure 7:
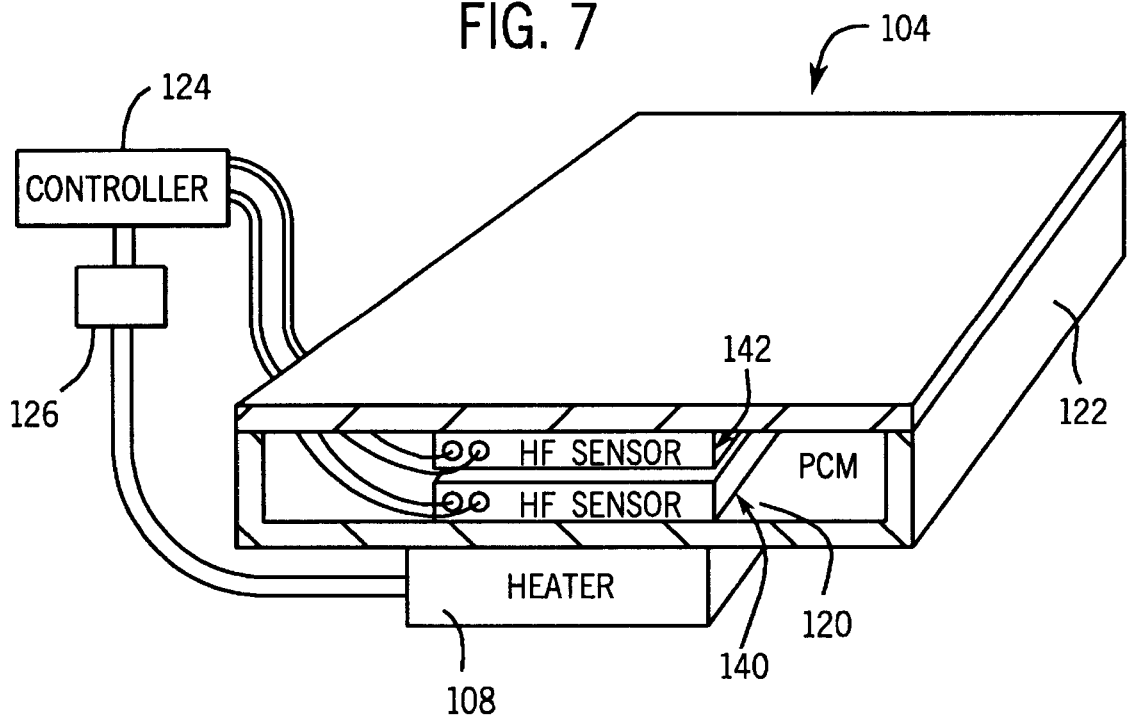
FIG. 7 is a cutaway side view of a phase control module constructed in accordance with a fourth embodiment of the invention.

Referring now to FIG. 3 and FIGS. 5 7, various embodiments illustrating control methods for monitoring the state of the phase change material 120 are shown. In each of these applications, a sensor 118 senses a parameter which provides an actual indication of the state of the phase change material. Control circuitry, such as that described above, compares the actual indication provided by the sensor to a set point, and adjusts the heater controller accordingly.

Referring first to FIG. 3, a temperature sensor 118 is provided in the phase change material 120. The temperature sensor 118 provides an indication of the actual temperature of the temperature control module 104, 106 during operation. When the phase change material 120 is in the phase change state, the actual temperature of the material 120 remains at a known, constant value. As the phase change material 120 solidifies, the temperature of the phase change material 120 drops without the addition of heat. Therefore, to maintain the detector 44 in an isothermal condition, heat must be added when a temperature drop is detected. Under these conditions, the heater controller 124 is activated to heat the phase change material, and the heat is controlled using a P, PI, PID, or other control loop as described above.

Referring now to FIG. 5, a second method for monitoring the phase change material is shown. This method relies on the fact that, as the phase change material changes state, the material will expand or contract, thereby increasing or decreasing the total volume in the sealed container or of the "air" space within (volume not filled with PCM). To detect these changes, the sensor 18 can be either a pressure transducer 130 or a strain gauge 132 coupled to the sealed vessel 122 (here pressure transducer is part of vessel volume) as the phase change material 120 changes phase, and the heater controller 124 selectively applies heat to the phase change material 120 to maintain the phase change material 120 within a predetermined percent phase change range. Empirical data stored in a look-up table or other database can be used to correlate the sensed parameters to the state of the phase change material. The pressure transducer 130 can also be used to sense the reduction of "air" space in the sealed vessel due to the expansion of the PCM. Although the term "air" has been used, any number of gases capable of achieving the desired result can be used to fill the volume not taken up by the PCM.

Figure 6:
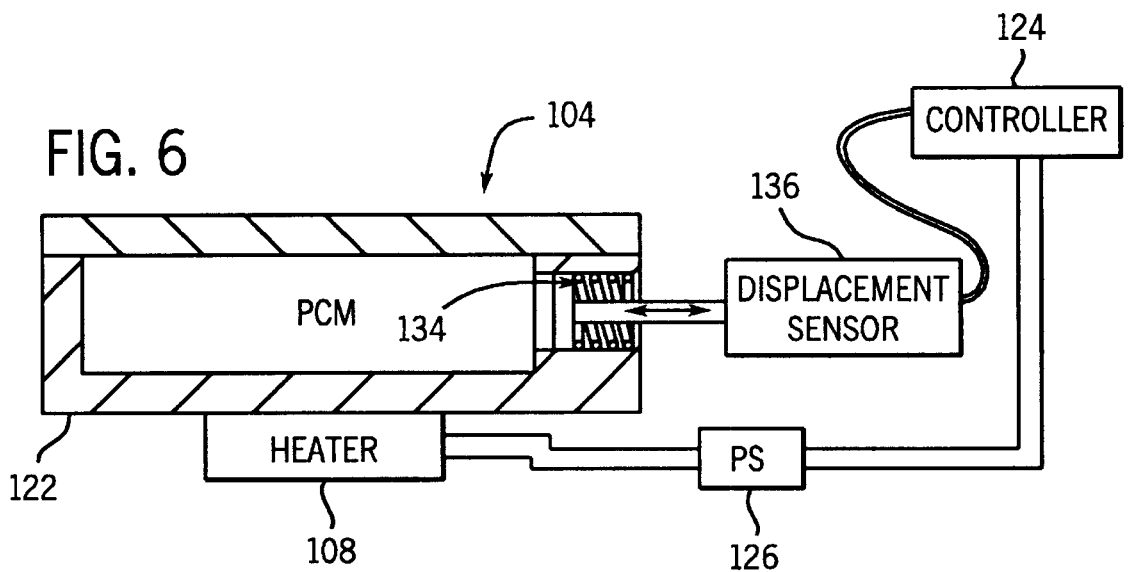
FIG. 6 is a cutaway side view of a phase control module constructed in accordance with a third embodiment of the invention.

Referring now to FIG. 6, in a third application, thermal expansion of the sealed vessel 122 is converted to secondary mechanical motion using a piston assembly 134. In this application, displacement of the sealed vessel 122 is measured using a displacement sensor 136 such as a linear variable differential transformer (LVDT), optical laser or Hall effect sensor. Again, the output of the sensor 136 is monitored to determine the change in the size or volume of the vessel 122. The amount of thermal expansion is then used by the heater controller 124 to determine the degree of phase change, and to provide data to a control loop. For example, a look-up table correlating known or empirically-derived thermal expansion parameters to phase change information could be used.

Referring now to FIG. 7, an alternative method in which the sensor 118 comprises heat flux sensors 140 and 142 coupled inside and at opposing sides of the sealed vessel 122 is shown. This control method relies on the fact that, as the phase change material 120 changes phase, the heat flux through the phase change material 120 varies for a given input. Therefore, a percent phase change is correlated to the difference between heat flux input and heat flux output, and this parameter is employed to control heat applied to the PCM module. Here, the heater controller 124 compares the input and output heat flux levels and, again, compares these to a set point which can be established empirically. The difference between the heat flux level is used to regulate the power applied to the heaters 108 and 110.

It should be understood that the methods and apparatuses described above are only exemplary and do not limit the scope of the invention, and that various modifications could be made by those skilled in the art that would fall under the scope of the invention. For example, although a construction in which multiple temperature modules and heaters has been shown, it will be apparent that various constructions including a single temperature module could be employed. Furthermore, although various specific temperature sensors have been described, it will be apparent that a number of methods for determining the state of the phase change module can be employed. To apprise the public of the scope of this invention, the following claims are made.

What is claimed is:

1. A detector assembly for use in a computed tomography scanner, the detector assembly comprising:

a detector array;

a phase change material coupled to the detector array;

a sensor, coupled to the phase change material, the sensor providing a signal indicative of the state of the phase change material;

a heating element, the heating element being coupled to the phase change material;

a controller device, the controller device being electrically coupled to control the heating element, wherein the controller device receives the signal from the sensor, compares the received signal to a selected set point value, and adjusts the heat supplied to the phase change material accordingly.

2. The detector assembly as defined in claim 1, wherein the heating element comprises a positive temperature coefficient heater.

3. The detector assembly as defined in claim 1, wherein the heating element comprises a thermoelectric cooler.

4. The detector assembly as defined in claim 1, wherein the sensor comprises a pressure sensor.

5. The detector assembly as defined in claim 1, wherein the sensor comprises a temperature sensor.

6. The detector assembly as defined in claim 1, wherein the sensor comprises a heat flux sensor.

7. The detector assembly as defined in claim 1, wherein the sensor comprises a strain gauge.

8. The detector assembly as defined in claim 1, wherein the sensor comprises a displacement sensor.

9. The detector assembly as defined in claim 1, wherein the phase change material comprises a paraffin.

10. A method for maintaining an x-ray detector array in an isothermal condition, the method comprising:

coupling a passive heat sink device comprising a phase change material to the detector array;

sensing a parameter indicative of a phase state of the phase change material;

comparing the parameter to a desired operating parameter, and selectively applying heat to the phase change material to maintain the parameter at the desired operating parameter.

11. The method as defined in claim 10, further comprising the step of coupling a heat conductive material along the length of the phase change material, the heat conductive material transferring heat along the length of the phase change material.

12. The method as defined in claim 10, further comprising the step of passively dissipating heat produced by the thermoelectric cooler.

13. The method as defined in claim 10, further comprising the step of actively dissipating heat produced by the thermoelectric cooler.

14. The method as defined in claim 10, further comprising the step of insulating the detector array to prevent heat produced by the X-ray tube from affecting the detector assembly.

15. A detector assembly for use in a computed tomography scanner, the detector assembly comprising:

a detector array;

first and second rails, the first and second rails disposed on opposing sides of the detector array;

a phase change material heat sink device coupled to each of the first and second rails;

a heater coupled to each of the passive heat dissipating devices;

a sensor coupled to the detector array;

a controller device, the controller device being electrically coupled to the sensor to receive a signal indicative of a state of the phase change material, the controller device comparing the received signal to a selected operational value, and supplying a command signal to the heater.

16. The detector assembly as defined in claim 15, wherein the sensor comprises at least one of a temperature sensor, a strain gauge, a displacement sensor, and a heat flux sensor.

17. The detector assembly as defined in claim 15, wherein the heater comprises a thermoelectric cooler.

18. The detector assembly as defined in claim 15, further comprising a heat tube coupled to the phase change material.

* * * * *